US006738653B1

(12) United States Patent
Sfez et al.

(10) Patent No.: US 6,738,653 B1
(45) Date of Patent: May 18, 2004

(54) METABOLISM MONITORING OF BODY ORGANS

(75) Inventors: Bruno Gad Sfez, Jerusalem (IL); Aner Lev, Modiin (IL); Zvi Kotler, Tel-Aviv (IL)

(73) Assignee: The State of Israel, Atomic Energy Commission, Soreq Nuclear Research Center (IL)

( * ) Notice: Subject to any disclaimer, the term of this patent is extended or adjusted under 35 U.S.C. 154(b) by 0 days.

(21) Appl. No.: 09/547,821

(22) Filed: Apr. 11, 2000

(30) Foreign Application Priority Data

Apr. 12, 1999 (IL) ................................................ 129398

(51) Int. Cl.⁷ ................................................ A61B 5/00
(52) U.S. Cl. ........................ 600/322; 600/310; 600/309
(58) Field of Search ................................ 600/309–310, 600/315–316, 322–328, 330, 336, 473–476, 320, 340

(56) References Cited

U.S. PATENT DOCUMENTS

| | | | | |
|---|---|---|---|---|
| 4,281,645 A | * | 8/1981 | Jobsis ........................ 600/324 |
| 5,174,298 A | | 12/1992 | Dolfi et al. |
| 5,212,667 A | | 5/1993 | Tomlinson, Jr. et al. ........ 367/7 |
| 5,286,968 A | | 2/1994 | Fournier et al. |
| 5,293,873 A | * | 3/1994 | Fang ........................ 600/437 |
| 5,299,570 A | * | 4/1994 | Hatschek ................... 600/479 |
| 5,529,065 A | * | 6/1996 | Tsuchiya .................... 600/310 |
| 5,553,610 A | * | 9/1996 | Lodder ....................... 600/310 |
| 5,833,602 A | * | 11/1998 | Osemwota .................. 600/310 |
| 5,865,167 A | * | 2/1999 | Godik ........................ 600/310 |
| 5,919,134 A | * | 7/1999 | Diab .......................... 600/323 |
| 5,951,481 A | * | 9/1999 | Evans ........................ 600/273 |
| 5,977,538 A | * | 11/1999 | Unger et al. ............. 250/227.2 |
| 5,987,351 A | * | 11/1999 | Chance ...................... 600/473 |
| 6,002,958 A | * | 12/1999 | Godik ........................ 600/407 |
| 6,041,248 A | | 3/2000 | Wang |
| 6,122,042 A | * | 9/2000 | Wunderman et al. ......... 356/73 |
| 6,128,525 A | * | 10/2000 | Zeng et al. ................. 600/476 |
| 6,201,989 B1 | * | 3/2001 | Whitehead et al. ......... 600/476 |
| 6,253,097 B1 | * | 6/2001 | Aronow et al. ............. 600/310 |

FOREIGN PATENT DOCUMENTS

| | | |
|---|---|---|
| DE | 44 19 900 A1 | 12/1995 |
| EP | 0 832 599 A1 | 4/1998 |
| WO | 94/28795 | * 12/1994 ............ A61B/6/00 |
| WO | 95/33987 | 12/1995 |

OTHER PUBLICATIONS

Kempe, M. et al., "Acousto–optic tomography with multiply scattered light," J. Opt. Soc. Am. A., vol. 14, No. 5, pp. 1151–1158 (1997).

Ishimaru, A., "Wave Progagation and Scattering in Random Media," Academic Press, pp. 62–69 (1978).

Seitz, P. et al., "Smart sensing using custom photo–application–specific integrated circuits and charge–coupled device technology," Opt. Eng., vol. 34, No. 8, pp. 2299–2308 (Aug. 1995).

(List continued on next page.)

Primary Examiner—Eric F. Winakur
Assistant Examiner—Matthew Kremer
(74) Attorney, Agent, or Firm—Lerner, David, Littenberg, Krumholz & Mentlik, LLP

(57) ABSTRACT

Method and apparatus for determining the oxygenation level of hemoglobin in a probed region of the human body. A probed region of the body is irradiated with diffuse light, the frequency of which is shifted with ultrasound focused at the probed region. The relation between the two states of the oxygenation of the hemoglobin is determined by the light absorption at the focal region of the ultrasound. The blood volume may be monitored by irradiating the probed region with light at the isosbestic point.

55 Claims, 9 Drawing Sheets

OTHER PUBLICATIONS

Spirig, T. et al., "The multitap lock–in CCD with offset subtraction," IEEE Transactions on Electron Devices, vol. 44, No. 10, pp. 1643–1647 (Oct. 1997).

Marks, F. et al., A comprehensive to approach to breast cancer detection using light: photon localization by ultrasound modulation and tissue characterization by spectral discrimination, General Electric Research and Development Center, Schenectady, N.Y., SPIE vol. 1888, pp. 500–510 (9/93).

Marks, F.A. et al., "A comprehensive approach to breast cancer detection using light: photon localization by ultrasound modulation and tissue characterization by spectral discrimination," SPIE, pp. 500–510, vol. 1888.

Leutz, W. et al., "Ultrasonic modulation of multiply scattered light," Physica B, pp. 14–19, vol. 204 (1995).

Wang, L. et al., "Continous–wave ultrasonic modulation of scattered laser light to image objects in turbid media," Optics Letters, Mar. 15, 1995, pp. 629–631, vol. 20, No. 6, Optical Society of America.

Kempe, M. et al., "Acoustic–optic imaging of absorbing structures with multiply–scattered light," Advances in Optical Imaging and Photon Migration, 1996, pp. 328–331, vol. 2, Optical Society of America.

Kempe, M. et al., "Acousto–optic tomography with multiply scattered light," J. Opt. Soc. Am. A., May 1997, pp. 1151–58, vol. 14, No. 5, Optical Society of America.

Wang, L. et al., "Ultrasound–modulated optical tomography of absorbing objects buried in dense tissue–stimulating turbid media," Applied Optics, Oct. 1, 1997, pp. 7277–82, vol. 36, No. 28, Optical Society of America.

Wang, L., "Ultrasonic Modulation of Scattered Light in Turbid Media and a Potential Novel Tomography in Biomedicine," Photochemistry an Photobiology, 1998, pp. 41–49, vol. 67(1), American Society for Photobiology.

Wang, L. et al., "Frequency–swept ultrasound–modulated optical tomography of scattering media," Optics Letters, Jun. 15, 1998, pp. 975–77, vol. 23, No. 12, Optical Society of America.

Mahan, G.D. et al., "Ultrasonic taggin of light: Theory," Proc. Natl. Acad. Sci. USA, Nov. 1998, pp. 14015–19, vol. 95, Applied Physical Sciences.

Leveque, S. et al., "Ultrasonic tagging of photon paths in scattering media: parallel speckle modulation processing," Optics Letters, Feb. 1, 1999, pp. 181–83, vol. 24, No. 3, Optical Society of America.

* cited by examiner

METABOLISM MONITORING OF BODY ORGANS

FIELD OF THE INVENTION

This invention relates to a process and apparatus for not invasively probing in real time oxygen metabolism in body organs by means of a combination of light and ultrasound.

BACKGROUND OF THE INVENTION

In recent years, much effort has been devoted to find ways to non-invasively probe regions of the brain, without using MRI or CT, which involve long procedures and do not allow real time analysis, except, to some extent, in some exceptional cases. Low-cost, portable and easy-to-use devices have been based on near infrared spectroscopy of blood, which have found some use by physicians. However, such techniques only provide a global picture of the brain without the minimum resolution which should allow a reliable diagnosis to be made.

Hemoglobin oxygenation gives an insight on the proper functioning of many body organs. This invention is particularly directed to probing hemoglobin oxygenation in the brain, but this is not intended as a limitation, and the invention includes probing in similar ways other organs, such as breast, liver, heart, and so on.

Light propagating inside a scattering medium has two components—ballistic and diffuse light. The first component does not experience scattering, while the second corresponds to strongly multi-scattered light (see M. Kempe, M. Larionov, D. Zaslatski and A. Z. Genack, *Acousto-optic tomography with multiply scattered light*, J. Opt. Soc. A., 14, 5, 1151 (1997)). Ballistic light decreases exponentially with distance in a scattering medium, whereas diffuse light remains roughly at the same relatively high intensity level. Therefore, diffuse light can give information to scattering medium deep inside it.

It is known in the art that information on the optical properties of the medium can be obtained by means of the said diffuse light, by focusing an ultrasound wave inside the medium at the particular region under examination. This phenomenon is exploited in U.S. Pat. No. 5,212,667 for the purpose of light-imaging in a scattering medium. Coherent light, generated as a laser beam and expanded by a beam expander, is projected into a scattering medium disposed between two parallel surfaces, in a direction perpendicular to said surfaces. Light emerging from it is a superposition of a multitude of scattered wavelets, each of which represent a specific scattering part. These wavelets are projected onto the viewing plane of a two-dimensional photodetector array, where they interfere with each other, giving rise to a speckle pattern. Propagating ultrasound pulses into the scattering medium in a direction substantially parallel to said surfaces, and focusing it in the probed region, changes the position of the scatterers and this causes a change in the speckle pattern. By comparing speckle images with and without ultrasound pulse, light absorption properties of the probed region can be measured. This method, however, based as it is on a unidirectional laser beam, has a limited capability of providing information on the scattering medium, and particularly, does not permit to obtain the information in real time as to hemoglobin oxygenation. Further, it does not permit to retrieve local hemoglobin oxygenation. U.S. Pat. No. 5,212,667 does not provide any algorithm showing how to retrieve such information. In fact, if only on-axis illumination is used, that is to say, the laser source, the ultrasound probe and the detector, are on the same line, modifying the position of the ultrasound probe does not allow to determine the local changes in absorption, because the absorption has to be integrated over the whole line.

If an ultrasound wave is focused inside a scattering medium and concurrently a continuous wave laser light beam crosses said medium and is strongly diffused thereby, light frequency is shifted by the ultrasound frequency (Doppler Effect) at the region of the focused ultrasound. At the other regions, the frequency of the light is practically unchanged, and consequently, the detection of the frequency-shifted light gives direct information on the optical properties of the region under test.

U.S. Pat. No. 5,212,667 is not concerned with changes in the speckle pattern. It states that, in the region in which the ultrasound is focused, the light-scattering properties are altered, owing either to change in the index of refraction induced by the pressure fluctuation of the ultrasound pulse, or by the changes in location of the scattering centers induced by such a pulse; and consequently, the speckle intensities in the focal plane are altered. The inventors submit that the magnitude of the speckle intensity change depends on the relative light absorption between the probed region and the surrounding medium. Other patents which refer to the tagging of light by the ultrasound are U.S. Pat. No. 5,174,298 and WO 95/33987. An article by Fay A. Marks et al, in SPIE, vol. 1888, p. 500, discusses the ultrasound tagging of light (UTL) as a tool for imaging breast tissue, and concludes that much work remains to be done to explore the feasibility of using UTL as a breast cancer imaging system.

SUMMARY OF THE INVENTION

The invention is based on the fact (see Ishimaru, A., *Wave Propagation and Scattering in Random Media*, Vol. 1, Academic Press (1978)) that hemoglobin can be found in the body in two different oxygenation states—oxyhemoglobin and deoxyhemoglobin—which have different light absorption spectra. In the near infrared (690 mm and above), the absorption coefficients of both states of hemoglobin are relatively low. At around 804 mm, both states have exactly the same absorption coefficient: this point is called "the isosbestic point". Therefore, measurement of blood absorption at this wavelength gives a direct indication of the blood volume being tested. At longer wavelengths, the absorption is essentially due to oxyhemoglobin. For example, at or around light wavelengths of 1 micron, the oxyhemoglobin absorbs more than three times than the deoxyhemoglobin: therefore, absorption at this wavelength gives a direct indication of the ratio between the two states of hemoglobin. The absorption spectra of oxyhemoglobin and deoxyhemoglobin are illustrated in FIG. 2.

The invention is characterized by the fact that the probed region (the part of the body in which the degree of hemoglobin oxygenation is to be monitored) is irradiated with light, preferably with a wavelength between 690 and 900 nm, the light frequency is shifted by an ultrasound pulse, and the degree of hemoglobin oxygenation is determined from the change in the absorption obtained at the frequency shifted signal.

FIG. 1 schematically illustrates the interaction between diffuse light and a focused ultrasound wave. An emitter emits light of frequency $\omega$ into the probed region. An ultrasound beam, of frequency $\Omega_{US}$ is focused onto the probed region. Ultrasound modulated light, having a shifted frequency $\omega+\Omega_{US}$, and non-modulated light having frequency ω are detected by a detector, which mixes them and generates a signal modulated at the ultrasound frequency. Hereinafter, the expression "modulated signal" will means the signal, detected by the detector, representing the intensity of the ultrasound modulated light, and expression "non-modulated signal" will means the signal, detected by the detector, representing the intensity of the light not modulated by the ultrasound. The word "signal" without specification, will include both the modulated and the non-modulated signal.

This invention, therefore, provides a method for determining the local oxygenation level of hemoglobin by comparing the absorption of an ultrasound frequency-shifted signal with the absorption of hemoglobin in different states of oxygenation, at several wavelengths. Diffuse light (optionally, but not necessarily, at the isosbestic point) experiences an absorption throughout regions of the body. If an ultrasound wave is focused in a part of the body, and the frequency of the light is changed, detectors outside the part of the body under examination can selectively detect the ultrasound-modulated light, viz. the light which has passed through the focal region of the ultrasound wave. The ratio between the modulated signal and the non-modulated signal is determined by the local absorption changes. The part of the body under examination, or "the probed region", may be, for example, the brain.

The invention also comprises optionally monitoring the blood volume by irradiating the probed region with light at the isosbestic point, detecting the light that is not absorbed, and determining the blood volume from the amount of light that is absorbed.

The method for determining the degree of oxygenation of hemoglobin, particularly comprises the steps of:

1—Irradiating the probed region with diffuse near-infrared light, preferably in the 690 to 900 nm wavelength range;
2—Generating at least an ultrasound wave, chosen from among continuous, pulse or burst waves;
3—Focusing said ultrasound wave in at least a region of the probed region;
4—Detecting light modulated by the ultrasound, originating from ultrasound focus region, for each light wavelength;
5—Determining the absorption of said modulated light by said probed region; and
6—Calculating from said absorption the degree of hemoglobin oxygenation in the probed region.

In a preferred embodiment of the invention, directed to monitoring the changes in the degree of oxygenation of hemoglobin in the probed region, the method comprises the steps of:

1—Irradiating the probed region with diffuse near-infrared light, preferably in the 690 to 900 nm wavelength range, using one or more wavelengths, but preferably two wavelengths, one below and one above the isosbestic point.
2—Generating at least an ultrasound wave, chosen from among continuous, pulse or burst waves;
3—Focusing said ultrasound wave in at least a region of the probed region;
4—Detecting light modulated by the ultrasound, originating from ultrasound focus region, for each light wavelength;
5—Determining the changes in the absorption of said modulated light caused by local changes in said probed region;
6—Calculating from said changes the changes of the degree of hemoglobin oxygenation in the probed region; and, preferably,
7—Shifting the focus of the ultrasound beam, whereby successively selecting different probed regions; and
8—Repeating for each successively selected probed region the determination of the change in the light absorption and in the degree of hemoglobin oxygenation.

Non-modulated light originating from the probed region is detected together with the modulated light. This is highly desirable in order to remove the influence of global changes in the probed region by a normalization algorithm, as will be explained hereinafter.

While the distinction between diffuse and ballistic light is well known, as has been set forth hereinbefore, it can be further clarified by considering the transmission of light through a scattering medium as a function of the thickness of the medium. In a transparent, non-scattering medium, all the light is ballistic. In a transparent, strongly scattering medium, ballistic light decreases exponentially very strongly and diffuse light decreases linearly. In a transparent, strongly scattering, slightly absorbing medium, ballistic light decreases exponentially very strongly and diffuse light decreases almost linearly, a slight exponential decrease due to absorption also occurring. Light in a scattering medium comprises, therefore, both ballistic and diffuse light. At low values of said thickness, the transmission signal decreases exponentially, but after a certain threshold, it decreases partially linearly and partially exponential, but the exponential component is relatively weak in the wavelengths considered herein, so that the decrease can be considered as substantially linear. Said threshold defines a ballistic regime below it, and a diffuse regime above it.

The change in the absorption of said ultrasound modulated light in the probed region, due to changes in the oxygenation state of the hemoglobin, is represented by an analog signal, that can then be transformed to a digital signal, to be processed and, if desired, visualized. The modulated signal is proportional to the amplitude of the light passing through the probed region, from which the absorption is calculated: the modulated signal changes reflect changes of the intensity of the light passing through the probed region, which in turn reflects changes in the absorption in the probed region. The signal has a frequency between a few hundred and a few MHz. It can be processed in various ways, e.g.: a) through a Lock-In Amplifier, which automatically detects the signal at the ultrasound frequency and transforms it into a digital signal which is sent to processor means; b) through an analog-to-digital card with a sampling cycle high enough to sample effectively the signal at the ultrasound frequency, the digitized signal being transferred to a computer memory and then processed in order to retrieve the signal at the ultrasound frequency; c) through a spectrum analyzer, which directly gives the signal at the ultrasound frequency.

Generally speaking, two kinds of blood circulation coexist in tissues: laminar circulation in large veins/arteries, which follows the heart rhythm, and capillary circulation in the tissues, which has a typical frequency of 0.1 Hz. In monitoring oxygenation changes, data are typically taken every minute. It is important that laminar circulation should not contribute heavily to the data signal. Since laminar circulation has only frequencies in the order of 0.1 Hz, viz. fast components relative to the frequency at which the data are taken, the contribution of laminar circulation to said data can be integrated out. It is integrated out because the integration is carried out over one or several minutes, which is a long period compared to the time periods associated with the laminar circulation.

DETAILED DESCRIPTION OF PREFERRED EMBODIMENTS

While the invention is broadly applicable to examining any part of the human body, in the embodiments of the invention, which will be particularly described, the probed region examined is the brain. However the brain has been chosen as a probed region merely for purposes of illustration and no limitation is intended by this choice. On the contrary, the description of the embodiments is sufficient to enable the application of the invention to any other part of the body, and while variations may be required for this purpose, persons skilled in the art are fully capable of determining them. Thus, higher ultrasound frequencies may be used, thereby obtaining better resolution and higher energy transfer, resulting in stronger signals. While the maximum ultrasound frequency for examining the brain is 1 to 2 MHz, for other parts of the body it may rise to about 8 MHz, and for special applications—e.g. high resolution or combination with hyperthermic ultrasound treatment—it may rise to about 16 MHz.

In carrying out the invention, both light and ultrasound waves must be simultaneously sent inside the probed region, which, as has been said, is assumed hereafter, for purposes of illustration, to be the brain. Since the main purpose of the system is to provide monitoring information, the sources as well as the detection system must be fixed on the head when the probed region is the brain. If the probed region is not the brain, the sources and the detection system will be placed in the appropriate position. The light is preferably laser light and is generated by at least one CW laser generator of the proper wavelength. Optical fibres, in bundles or not, can be directly set in the appropriate position, e.g. on the head, with, if necessary, an index matching substance for better light couplings. The light emerging from the probed region is collected through coupling devices by fibre bundles linked to the detection system, which is preferably based on a multi-channel input detector, such as a CCD camera or photomultipliers array. It should be understood that, whenever the use of a "camera" is mentioned in this application, a single or several detectors can be used in alternative to it, so that the word "camera" should be construed as including such alternatives, even when this is not mentioned. The ultrasound wave is produced by a transducer or a transducer array tightly pressed against the part of the body under examination, in the following examples against the skull.

Figure 1:
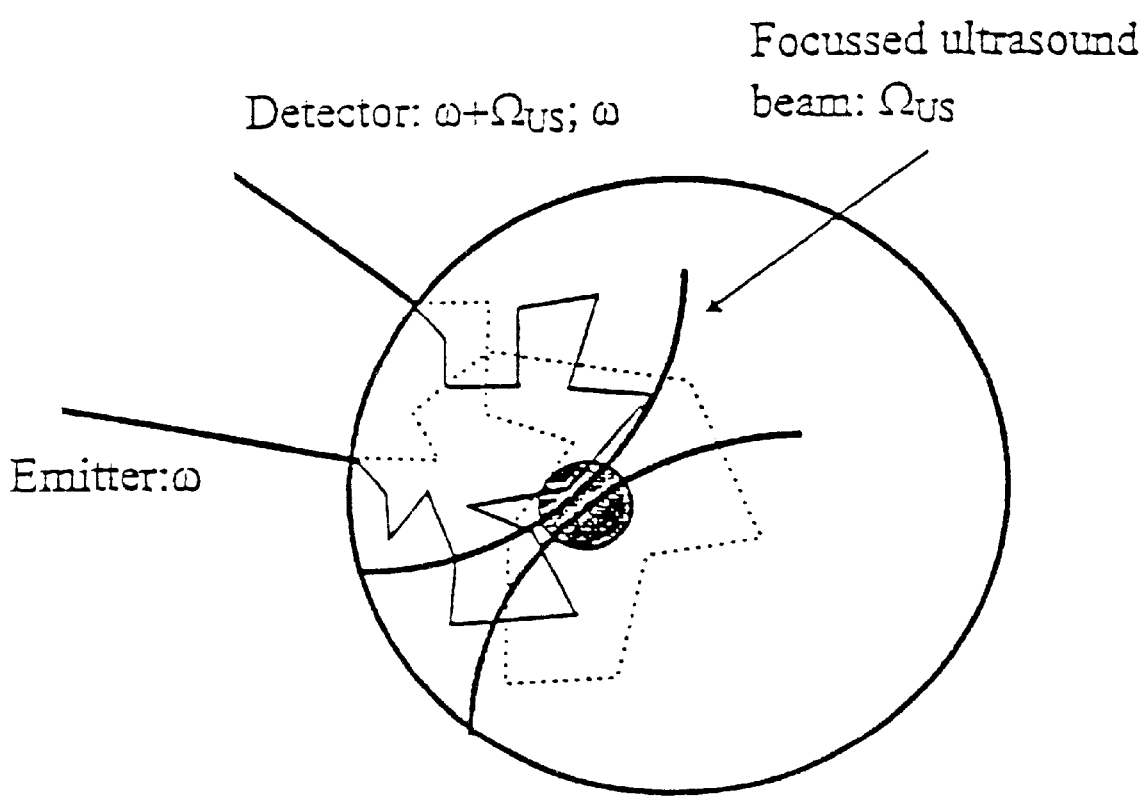
FIG. 1 schematically illustrates the interaction between diffuse light and a focused ultrasound wave.
Figure 2:
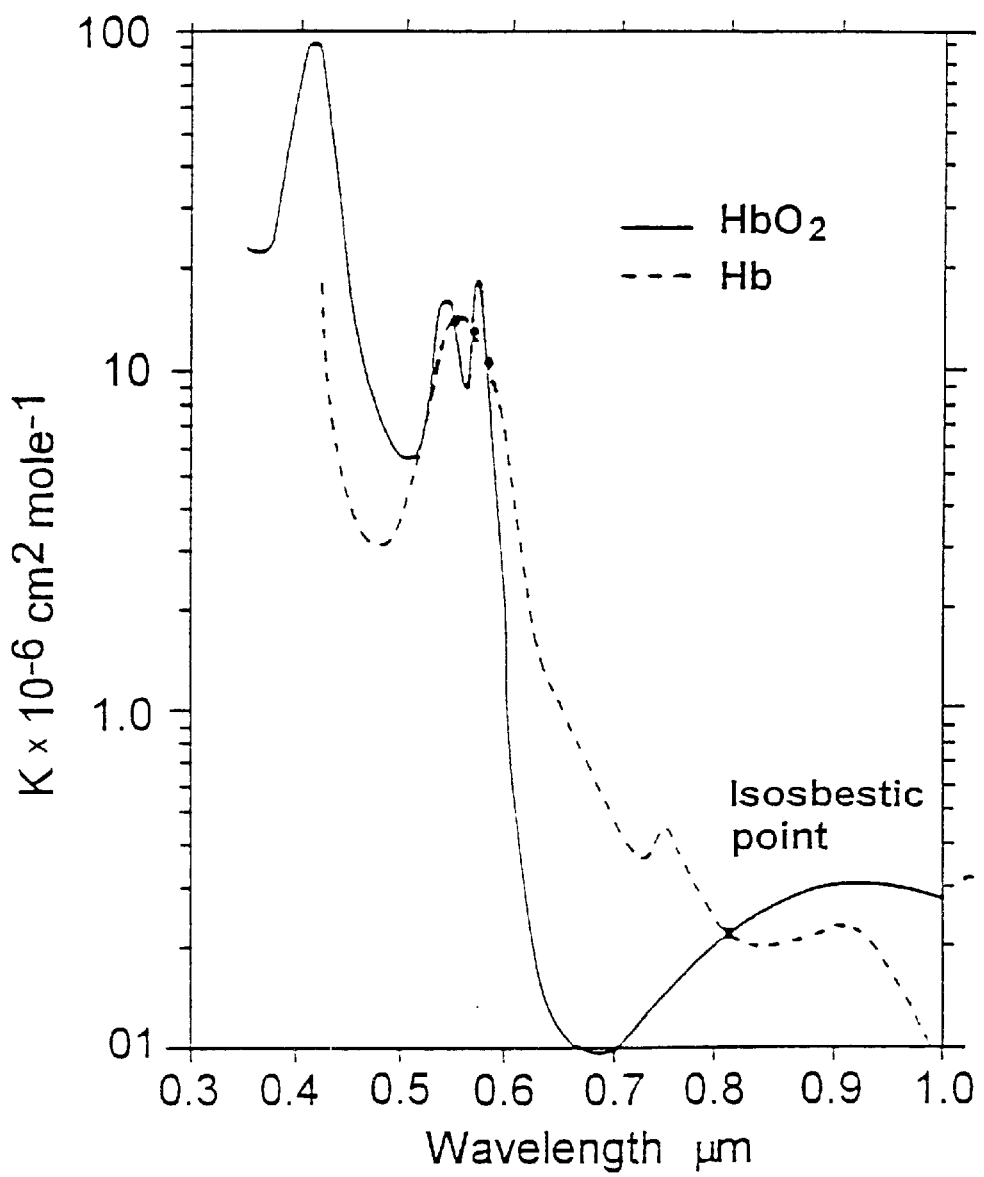
FIG. 2 shows the absorption spectra of oxyhemoglobin and deoxyhemoglobin.
Figure 3:
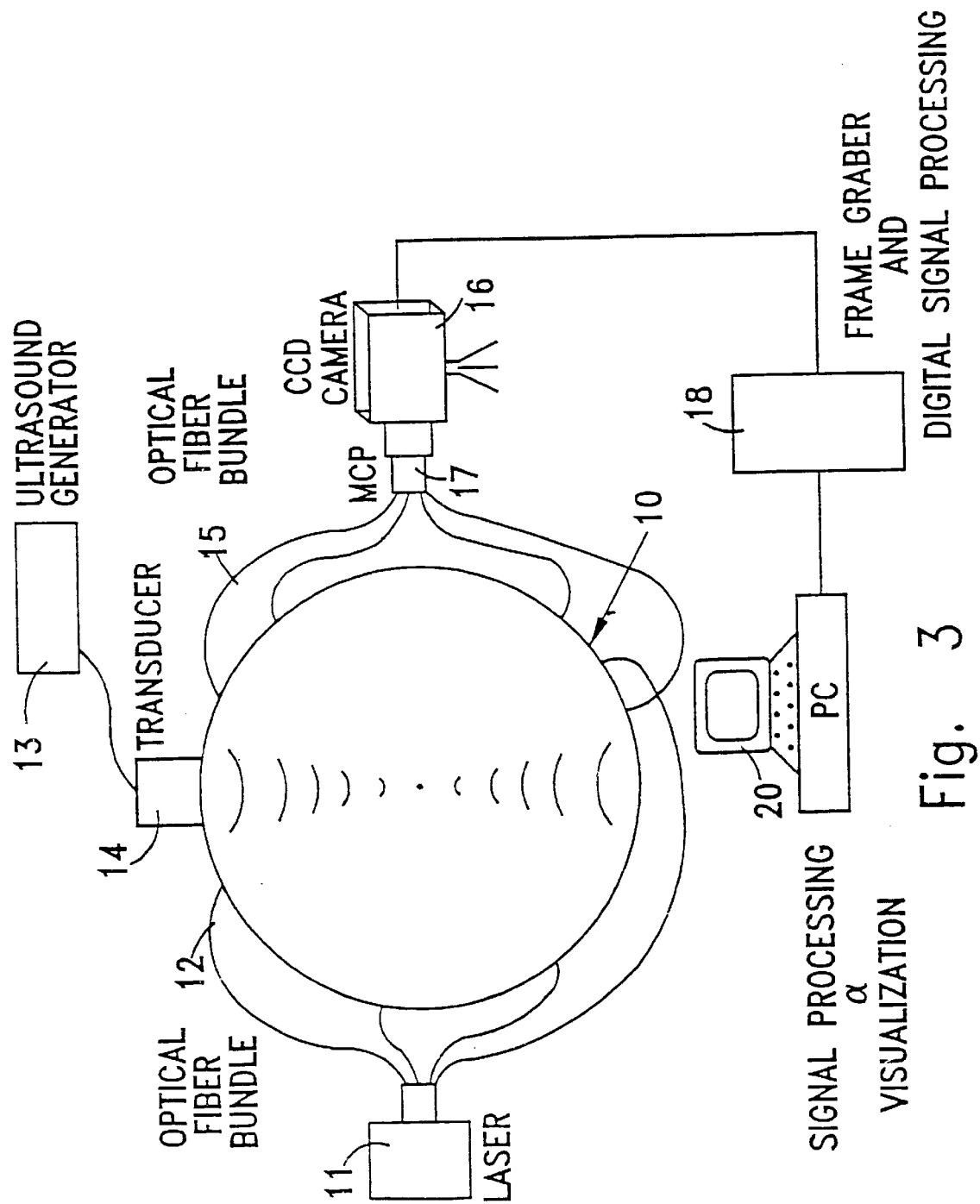
FIG. 3 schematically represents an apparatus according to an embodiment of the invention.

FIG. 3 schematically represents an apparatus according to an embodiment of the invention. Numeral 10 indicates the part of the body that is to be examined, in this particular case a cranium. Numeral 11 indicates a laser generator, that is optically connected to skull 11 by optical fibre bundles 12 and coupling devices, not shown. 13 is a voltage generator designed for ultrasound use and 14 a transducer which generates the ultrasound. Numeral 15 indicates other optical fibre bundles, which collect, through coupling devices, not shown, the light that has passed through the probed region and transmit it, through a multi-channel plate (MCP) 17, to a receiving instrument, in this case a CCD camera 16 or other detector array. Alternatively, the signal can be sent to a photomultiplier, or an array of photomultipliers, or a diode detector. The camera is connected to a frame grabber and digital signal processor 18, and this latter transmits its signals to a signal processor and visualizing apparatus 20, which can be a PC.

The ultrasound wave generated by generator 13 can be pulsed, continuous or burst. Its frequency lies between 0.2 and 2 MHz, the boundaries being set by the size of the focal region (lower frequencies) and by the penetration of the ultrasound wave through the skull (higher frequencies), lower frequencies producing larger focal region sizes and higher frequencies produce less penetration of the tissues.

The advantage of the CW ultrasound generation over the pulsed generation consists essentially in a better signal to noise ratio. Moreover, since the light beam is focused, reflections from the tissue/air interface, which would interfere in case of non-focused beam, are here negligible.

Figure 4:
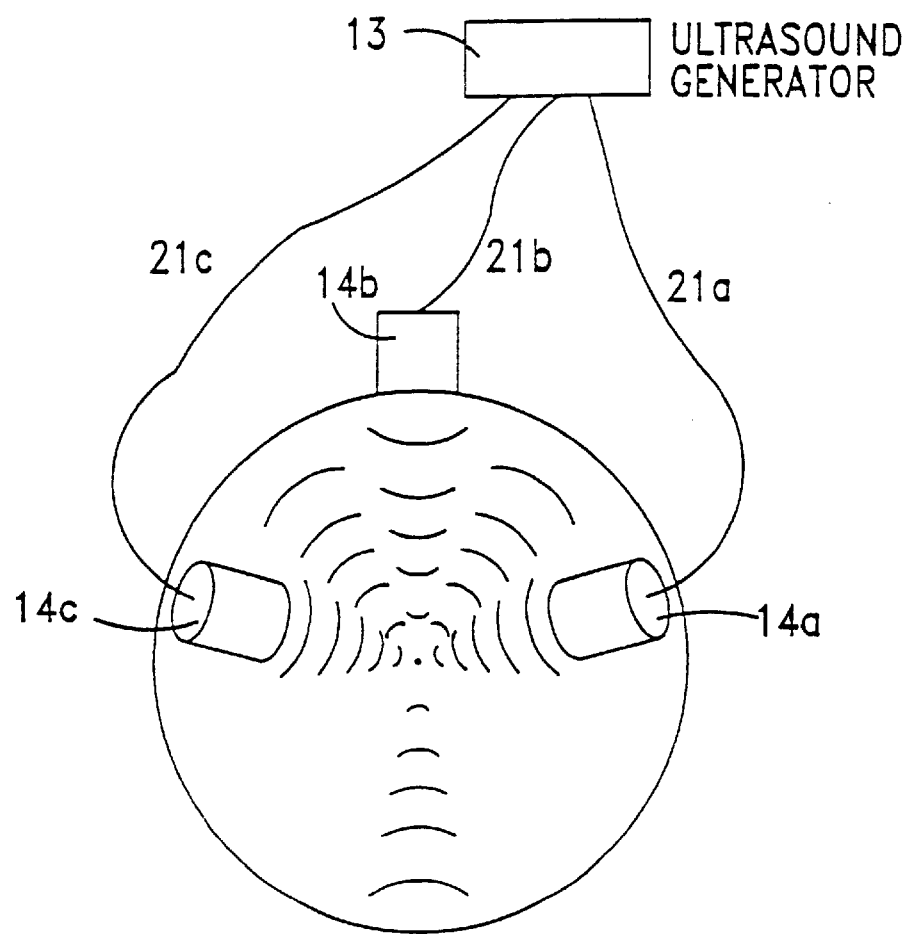
FIG. 4 schematically represents an alternative embodiment of the invention.

In an alternative embodiment of the invention, illustrated in FIG. 4, the ultrasound wave, generated at 13, is transmitted through different channels 21a, 21b 21c, etc., to different transducers 14a, 14b 14c, etc., spread over a large region of the skull, arranged so that the ultrasonic waves of each of the transducers are focused in the same region on the brain, or so that the ultrasonic waves of each of the transducers are phase-arrayed to produce a strong focus in the brain. Bones typically absorb ultrasound waves 17 times more that brain tissue (see Ishimaru, A., *Wave Propagation and Scattering in Random Media,* Vol. 1, Academic Press (1978)). In imaging (echo) applications, ultrasound is usually made to enter the skull through a small number of regions on the skull where the bone is locally thinner (moreover, in those applications, not only the incident ultrasound wave but also the reflected wave crosses through the skull, which means that the effective signal attenuation is 17×17=289). In the method of this invention, imaging is not a requirement, and thus, the reflected signal do not matter. Each transducer can then can feed a relatively large amount of power to the brain. Although a large amount of this power is absorbed in the skull, the large number of transducers compensate for it at the common focusing region. Considering, for example, the case in which three transducers are used, the effective energy that each transducer has to transmit into the skull is 17×3≈50 times lower than what is required for echo measurements.

Several different characteristics of the light must be taken into consideration in carrying out the method of this invention. Particularly, they comprise:

I—The nature of the light (wavelength, coherence length, noise, etc).

II—The inlet and the outlet of the light into and out of the head, as well as its distribution inside the brain.

III—Heterodyning
I—Nature of the Light

Because of lower absorption from the blood and lower scattering efficiency, in this invention it is preferred to use light in the wavelength range 690 nm–900 nm. The coherence length of the light beam is at least one meter, in order to get the best speckle contrast. Multimode operation of diode laser is possible, as long as hopping from mode to mode occurs at frequencies lower than the ultrasound frequency. The contrast will be lower by a factor of $n^{1/2}$, where n is the mode number. By "contrast" is meant herein the amplitude of the modulation of the ultrasound modulated light intensity divided by the DC intensity II—Inlet and Outlet of the Light and Light Distribution Inside the Brain Optical fibres are used for introducing the light into the skull and collecting the light from it. Good light distribution inside the brain produces better results. In order to assure such a good light distribution, one can use a number of optical fibre bundles distributed over the skull, around the region under test. Light transmission into and from the skull can be improved by using an index matched gel (gel having an index of refraction around 1.4).

III—Heterodyning is Preferably Resorted to in Carrying Out the Invention.

There are two possible ways to create the heterodyne signal, that will be referred to hereinafter as "detection modulation" and "source modulation".

Figure 5:
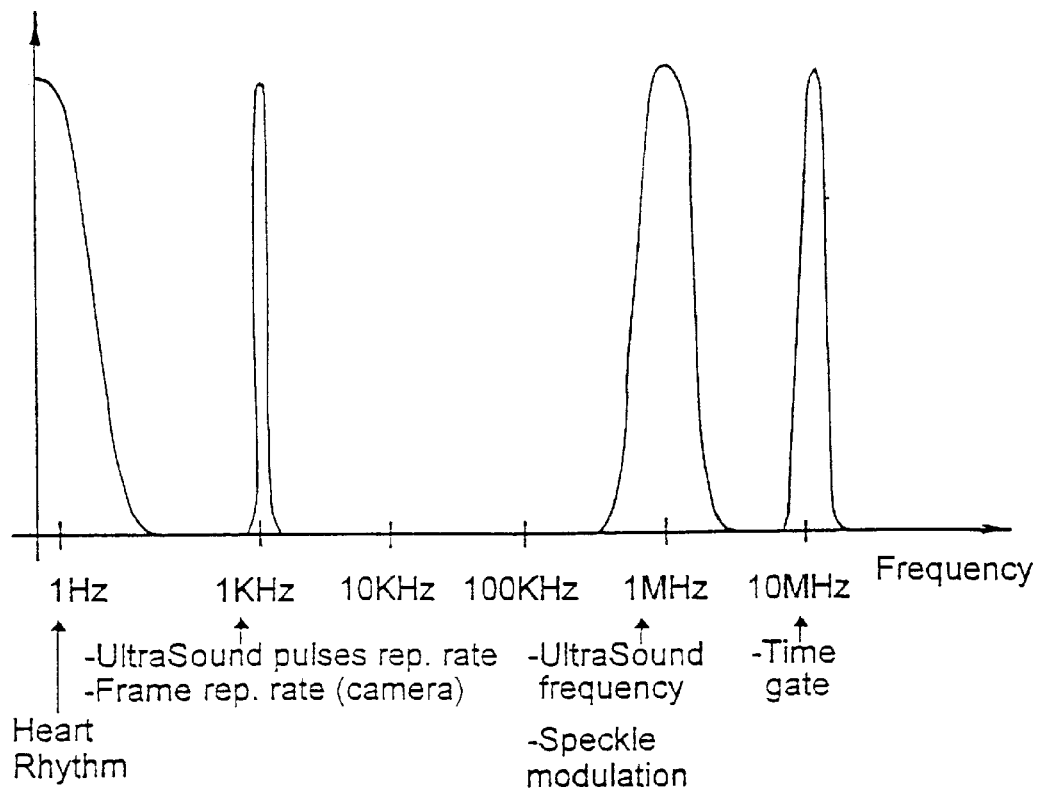
FIGS. 5, 6 and 7 schematically illustrate the detection modulation, source modulation and time sampling techniques, respectively.

Detection modulation is illustrated in FIG. 5, in which the abscissa is the frequency of the modulating ultrasound and the ordinate is the intensity of the detected modulated light. This illustration is only schematic, as the scale is not correct, but it gives an adequate idea of the frequencies involved. In such modulation, the light is sent across the head prior to being frequency shifted. The light which interacts with the ultrasound becomes frequency shifted around the ultrasound modulation frequency of the light. FIG. 5 refers to different frequencies that are involved in the detection process:

below 10 Hz, heart related phenomena around 1 KHz, repetition rate of the ultrasound pulses (in case of pulsed/burst operation)

around 1 MHz, ultrasound modulation around 10 MHz, time gating of the detector (or time resolution of the detecting system).

The light detected after it has traversed the brain forms a complex speckle pattern composed of three main components:

Speckle due to the interference of light at frequency $\omega_L$ (original light frequency) with itself, which is a static speckle (not changing in time).

Speckle due to interference of the frequency shifted light, at frequency $\omega_L + \Omega_{us}$ (where $\omega_{us}$ is the ultrasound frequency) with itself, which is a static speckle.

Speckle due to interference of light at $\omega_L$ and light at $\omega_L + \Omega_{us}$. This speckle is modulated at the frequency $\Omega_{us}$. It corresponds to an auto-heterodyning of the light itself, and appears at the ultrasound frequency. This is the signal which contains the information that the method of the invention is meant to obtain. Homodyne detection at $\Omega_{us}$ allows to detect the heterodyned signal.

If modulated and non-modulated signals originating from the same probed region are detected, they will both remain at the same level if there is no change in the absorption of said region. If there is some change, both signals will change, viz. decrease/increase, however not to the same extent. If the absorbing region is located at the focal point of the ultrasound wave, the modulated signal will decrease/increase strongly, while the non-modulated signal will decrease/increase only slightly. This is due to the fact that the absorbing region fills the ultrasound modulated focus, but is far from filling the whole volume of the probed region.

However, if the absorbing region is not located at the ultrasound focus, then the decrease/increase of the modulated signal will be only marginal, in fact, will occur at the same rate as that of the non-modulated signal.

To put things more quantitatively, and assuming one absorbing region B and one detector detecting one single speckle area, we can divide the whole probed region A into the absorbing region B where the ultrasound focus is present, and the region A-B where the ultrasound is not present (or at least very weak). On the detector surface, the not-Doppler-shifted and the Doppler-shifted intensities are $I_1$ and $I_2$ respectively.

In the heterodyning arrangement, the detector detects two signals:

One is the non-modulated signal, obtained using either the DC component of the signal spectrum, or, directly, by integrating the signal over a "long" time (long means several ultrasound cycles).

The other is the modulated signal, which is obtained by heterodyning of the Doppler-shifted and not-Doppler-shifted signals.

This can be seen mathematically in the following way. The total intensity detected by the detector is:

$$I = K|E_1 e^{i(\omega_L t + \phi_1)} + E_2 e^{i(\omega_L + \Omega)t + \phi_2}|^2,$$

where $E_1 e^{i(\omega_L t + \phi_1)}$ represents the non-Doppler-shifted field impinging on the detector, whereas $E_2 e^{i(\omega_L + \Omega)t + \phi_2}$ represents the Doppler-shifted field.

The intensity can be rewritten:

$$I = (I_1 + I_2 + 2KE_1 E_2 \cos(\Omega t + (\phi_2 - \phi_1))),$$

where $I_1 = K|E_1|^2$, and $I_2 = K|E_2|^2$. $I_1 \ll I_2$ (the Doppler-shifted intensity is much smaller than the non-Doppler-shifted intensity).

The non-modulated signal on the detector is $S_{nm} = I_1 + I_2$.

The modulated signal is $S_m = 2KE_1 E_2$ (which is sampled at the ultrasound frequency $\Omega$). This signal is the heterodyned signal.

The ratio of the modulated to the non-modulated signal is thus $2KE_1 E_2 / (I_1 + I_2)$. Since $I_2$ is much smaller than $I_1$, this can be rewritten $$S_m / S_{nm} = 2E_2 / E_1 = \Delta 2 (I_2 / I_1)^{1/2}.$$

Taking the logarithmic derivative, one obtains:

$$\Delta S_m / S_m - \Delta S_{nm} / S_{nm} = I_2 / I_2 - \Delta I_1 / I_1.$$

Let us now evaluate $\Delta I_2 / I_2 - \Delta I_1 / I_1$.

The non-Doppler-shifted intensity impinging on the detector can be written:

$$I_1 = C_1 I_0 \eta_A,$$

where $C_1$ is a coefficient taking into account the attenuation of the intensity due to scattering only from the source to the detector, $I_0$ is the source intensity and $\eta_A$ is the attenuation of the intensity due to the absorption.

Similarly, the Doppler-shifted intensity impinging on the detector can be written:

$$I_2 = C_2 I_0 \eta_{A-B} \eta_B,$$

where $C_2$ is a coefficient taking into account the attenuation of the intensity due to scattering only from the source to the detector, $I_0$ is the source intensity, and $\eta_{A-B}$ is the attenuation of the intensity due to the absorption in the A-B region and $\eta B$ is the attenuation of the intensity due to the absorption in the B region. This is due to the fact that modulated light necessarily passes through the region B (which is where the ultrasound focus lies).

Let us take the logarithmic derivative of both intensities, $$\Delta I_1/I_1 = \Delta \eta_A/\eta_A$$

$$\Delta I_2/I_2 = \Delta \eta_{A-B}/\eta_{A-B} + \Delta \eta_B/\eta_B.$$

These formulae assume essentially that small changes in absorption do not change the scattering properties of the tissues. Since the B region is considered as small compared to the A region (at least ten times smaller in volume), $\Delta \eta_{A-B}/\eta_{A-B}$ can be assimilated to $\Delta \eta_A/\eta_A$. Replacing these expressions into the one above, one finally finds that:

$$\Delta U_2/I_2 - I_1/I_1 = \eta_B/\eta_B.$$

Let us now evaluate $\Delta 72_B/\eta_B$.

We can write $\eta_B = \exp -\alpha_B L$, is a length associated to the mean path that the photons spend in the B region due to scattering (L is larger than the B region diameter in general), and $\alpha_B$ is the local absorption in the B region (probed region). Taking the logarithmic derivative, one finds:

$$\Delta \eta_B/\eta_B = -\Delta \alpha_B L.$$

Finally, one finds, for a given wavelength $\lambda$, that:

$$-\Delta \alpha_B(\lambda)L = (\Delta S_m/S_m - \Delta S_{nm}/S_{nm})(\lambda).$$

This, in turn, can be related to the oxygen saturation, if the measurement is done at two wavelengths (at least):

$$\Delta \alpha_B(\lambda_1)L = \{\Delta n_{ox}\alpha_{ox}(\lambda_1) + \Delta n_{deOx}\alpha_{deOx}(\lambda_1)\}CL$$

$$\Delta \alpha_B(\lambda_2)L = \{\Delta n_{ox}\alpha_{ox}(\lambda_2) + \Delta n_{deOx}\alpha_{deOx}(\lambda_2)\}CL,$$

where $\Delta n_{ox}$, $\Delta n_{deOx}$ are the changes in the oxy and deoxyhemoglobin concentrations, C is a proportionality factor, $\alpha_{ox}(\lambda_i)$ is the absorption of the oxyhemoglobin species at $\lambda_i$, and $\alpha_{deOx}(\lambda_i)$ is the absorption of the deoxyhemoglobin species at $\lambda_i$.

From these formulae, one finds:

$$CL\Delta n_{ox} = [L\Delta \alpha_B(\lambda_1)\alpha_{ox}(\lambda_2) - L\Delta \alpha_B(\lambda_2)\alpha_{ox}(\lambda_1)]/[\alpha_{ox}(\lambda_2)\alpha_{deOx}(\lambda_1) - \alpha_{ox}(\lambda_1)\alpha_{deOx}(\lambda_2)]$$

$$CL\Delta n_{deox} = [L\Delta \alpha_B(\lambda_1)\alpha_{deox}(\lambda_2) - L\Delta \alpha_B(\lambda_2)\alpha_{deox}(\lambda_1)]/[\alpha_{ox}(\lambda_2)\alpha_{deOx}(\lambda_1) - \alpha_{ox}(\lambda_1)\alpha_{deOx}(\lambda_2)]$$

The oxygen saturation OS change $\Delta OS$ is given by $\Delta n_{ox}/(\Delta n_{ox} + \Delta_{ndeOx})$:

$$\Delta OS = [L\Delta \alpha_B(\lambda_1)\alpha_{ox}(\lambda_2) - L\Delta \alpha_B(\lambda_2)\alpha_{ox}(\lambda_1)]/[L\Delta \alpha_{ox}(\lambda_2) + \alpha_{deOx}(\lambda_2)) - L\Delta \alpha_B(\lambda_2)(\alpha_{ox}(\lambda_1) + \alpha_{deOx}(\lambda_1))]$$

where $L \Delta \alpha_B(\lambda) = -(\Delta S_m/S_m - \Delta S_{nm}/S_{nm})(\lambda)$, and $\alpha_{ox}(\lambda)$, $\alpha_{deOx}(\lambda)$ are known data.

It appears from these last two equations that:

the determination of the oxygen saturation does not require the knowledge of the size of the probed region;

if the illumination is more or less homogeneous, without strong shadowing, the medium A does not have to be homogeneous;

the saturation obtained is an absolute number, which gives the possibility of mapping the saturation inside a given body region.

If we now consider the case that the region A-B is not homogeneous, viz. that the volume A comprises several absorbing regions $B_i$, which are, for example, successively probed by the ultrasound, the conclusions drawn from the case of a single B region remain valid, as long as none of the absorbing $B_i$ regions is "shadowing" another of such regions. If only one source of light and one detector are present, then an absorbing region $B_{i1}$ between another absorbing region $B_{i2}$ and the detector would "shadow" the absorption changes in the $B_{i2}$ region and make them difficult to detect. By using several sources and/or several detectors, it is possible to remove this shadowing, and apply the rules derived above as generally valid rules.

Figure 6:
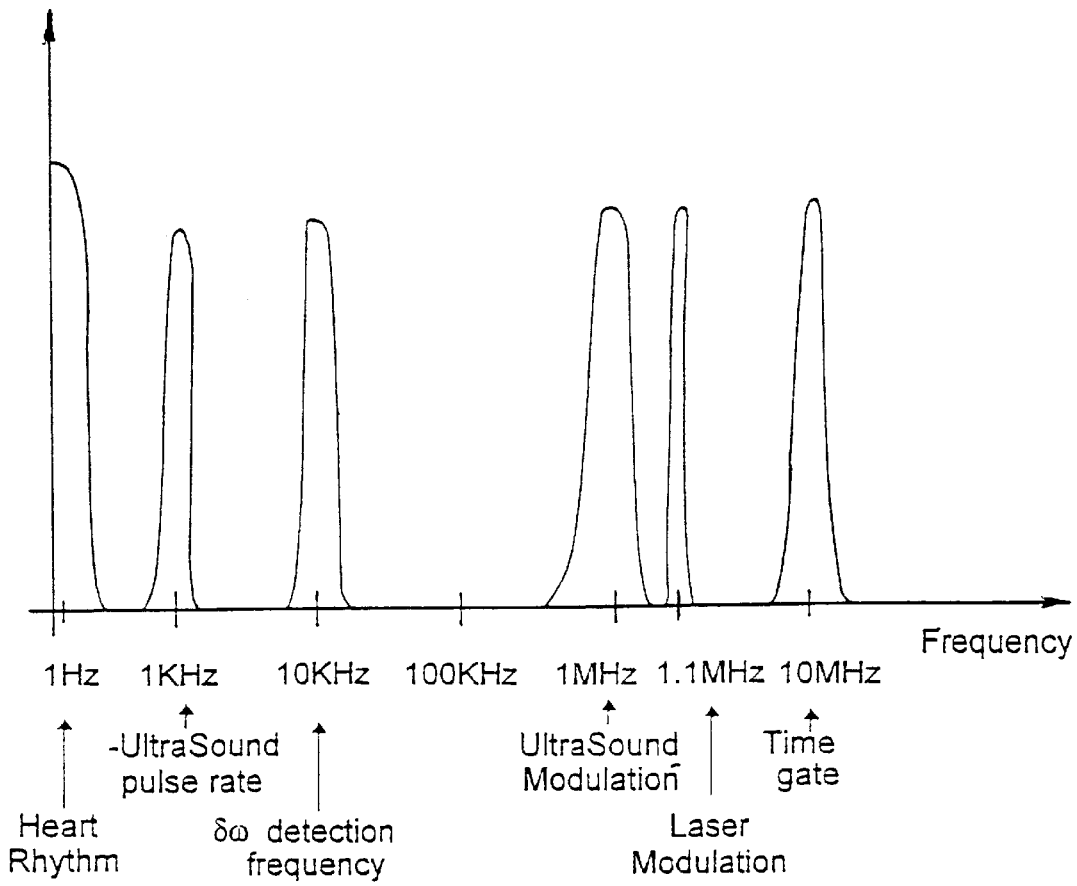

Source modulation is schematically illustrated in FIG. 6. In this scheme, the light is frequency shifted using for example a rotating grating (see L. E. Drain, The Laser Doppler Technique, Wiley Interscience(1980) pp. 166–167) at a frequency $\Omega_{us} + \delta\omega$, where $\delta\omega$ is a small frequency compared to the ultrasound frequency $\Omega_{us}$. One obtains from the modulator the non-diffracted beam (zero order light) as well as several orders of diffraction. If the higher orders are ignored, there is obtained the superposition of three beams:

the zero order beam at frequency $\omega_L$ the order +1 beam at the frequency $\omega_L + \Omega_{us} + \delta\omega$ the order−1 beam at the frequency $\omega_L - \Omega_{us} - \delta\omega$ The light is sent across the head. Part of the light interacts with the ultrasound, which gives to each of the laser frequencies shifts of $\pm\Omega_{us}$. Thus there are six slightly different laser frequencies exiting the head. They interfere on the detector and give 36 contributions (18 positive and 18 negative frequencies), among which some are at the same beating frequency. The most important contributions are those which contain at least one of the components deriving from laser light not interacting with the ultrasound region (since this region is small and relatively few photons cross through it). The said components can be classified into 2 kinds: a) laser light not frequency shifted by ultrasound and interfering with itself: heterodyning at frequencies 0, $\Omega_{us} + \delta\omega$, and $2(\Omega_{us} + \delta\omega)$;

laser light not frequency-shifted by ultrasound and interfering with ultrasound frequency-shifted light: heterodyning at frequencies $\delta\omega$, $\Omega_{us}$, and $2\Omega_{us} + \delta\omega$.

Thus a band-pass detection around $\delta\omega$ gives the desired information, as will be further explained.

The two aforesaid methods are aimed at different uses. Detection modulation allows fast sampling rate (typically, at 1 MHz ultrasound frequency, it is possible to get a 1 KHz sampling rate, assuming integration of 1000 pictures for each point). This allows almost real time mapping of the brain, or of other region of interest. The disadvantage of the technique is the fast (1 KHz or so) sampling rate, requiring fast camera and fast digital processing.

In contrast, source modulation is a much slower technique. For example, if $\delta\omega$ is chosen to be 50 KHz, the same integration over 1000 pictures gives a sampling rate of 50 Hz. This does not allow real time mapping. However, for most brain monitoring applications, where one picture every 30 seconds is enough, this technique is suitable. Another advantage thereof is that it requires only a regular camera and conventional digital signal processing, which reduces the system cost. It is also advantageous in applications where the ultrasound frequency is higher (such as non-brain applications where the ultrasound frequency spans the range of 5 MHz to 8 MHz, or ultrasound based operations where the frequency can reach 16 MHz).

The detection of the signals issuing from the probed region will now be discussed. As has been set forth before, the image pattern resulting from said signals is a superposition of several speckle images, which are modulated at different frequencies. The main purpose of the detection system is to pick up the proper signals at the proper frequency and get rid of the remaining signals, which contribute to the noise. Two detection techniques will be described: the time sampling technique and the lock-in CCD technique.

Figure 7:
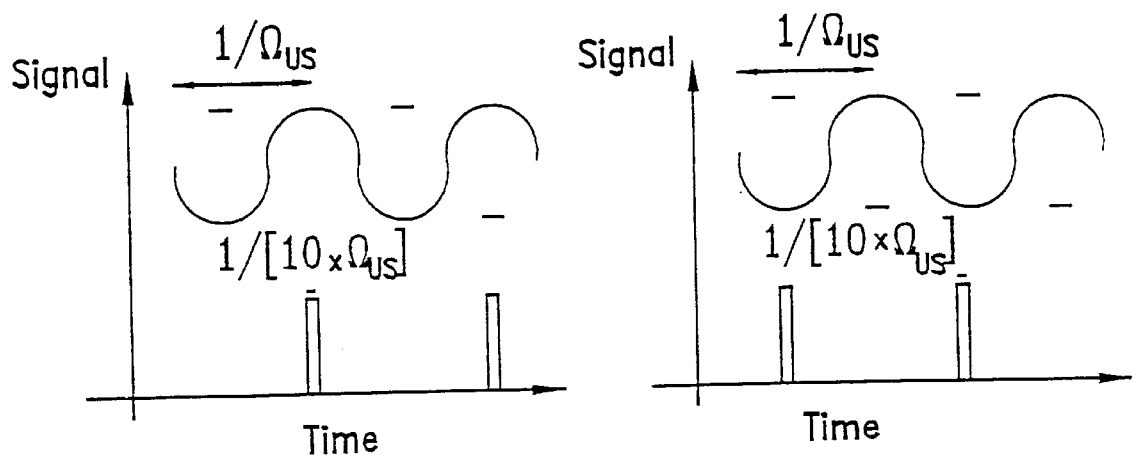
Figure 7:
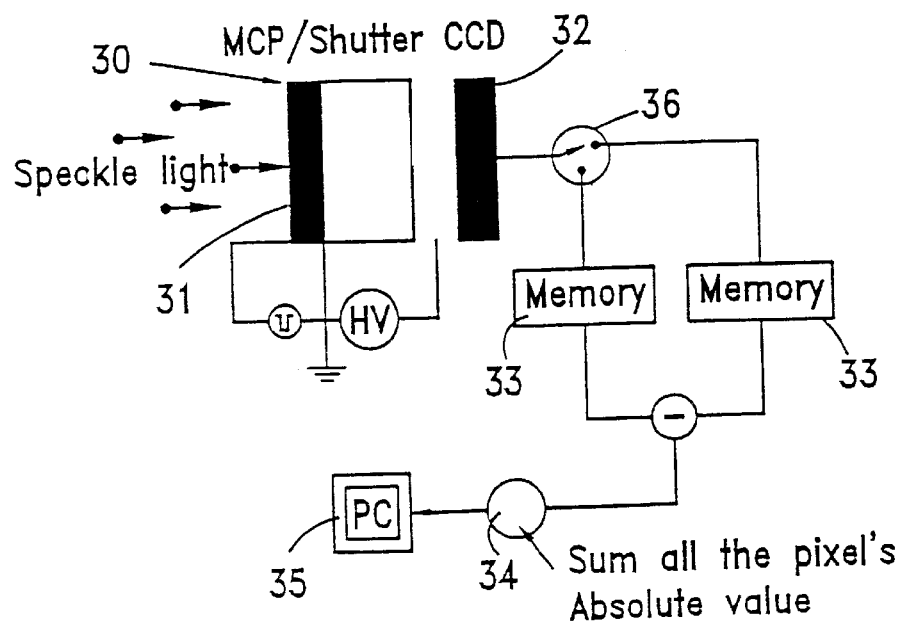

The time sampling technique is schematically illustrated in FIG. 7. The basic idea underlying this technique is to record the speckle image synchronously with the frequency that it is desired to pick up. This is done using a short gate which opens synchronously with said frequency. The time during which the gate remains open is short enough so as to avoid integration of the modulated signal over the whole cycle, but is long enough to integrate the signals coming from higher frequencies. Typically, the gate should be opened one tenth of the cycle duration.

In this technique, light emerging from the probed region, in this example the skull passes through a multi-channel plate (MCP) gated amplifier, generally indicated at 30 and provided with a shutter 31, which determines the time during which the gate remains open, towards a CCD camera 32 with at least 12 bits resolution. The speckle signal is imaged to the CCD detector (via the MCP) so that the average coherence zone of the speckle has the size of the CCD pixel. This is in order to minimize the average of the modulated signal, which is reduced like $N^{-\frac{1}{2}}$, where N is the number of coherence zones per pixel. The role of the MCP is twofold: increase the signal intensity and provide a fast gate. It should be noted that if the signal is high enough in the case of source modulation, there is no need for the MCP and a simple mechanical or electronic shutter (for example the camera shutter) is enough for the detection. Numeral 33 indicates memory means to which the pixel values are alternatively transmitted through switch 36. 34 is an adder, which sums all the pixels' absolute values, and 35 designates processing means, such as a PC.

The MCP is gated synchronously with the ultrasound wave $\Omega_{us}$ (detection modulation) or with the frequency shift $\delta\omega$ (source modulation) during a time that is short compared to one ultrasound cycle duration (typically $1/(10\Omega_{us})$. The opening of the gate being in phase with the ultrasound, the picture which falls on the camera is the same at each cycle. Said picture can be integrated during a long time, provided that the CCD camera is left open during this time. The noise is then reduced by a factor $M^{-\frac{1}{2}}$, where M is the number of pictures integrated by the camera. After a given integration time $\tau$, the picture from the camera is transferred to a frame grabber where it is stored.

Then the same procedure is repeated at a $\tau$ phase-shift, and the new image is again sent and stored in the frame grabber. The frame grabber digitally subtracts one picture from the other, which gives a new picture of the local amplitudes of the modulated signal. Then all the absolute values if the amplitudes are summed. This number is the average amplitude of the modulation.

The upper portion of FIG. 7 shows the principle of the MCP gate timing as compared to the ultrasound cycle timing. The left part shows the ultrasound wave (as a function of the time) and below it, the opening of the gate (or the laser pulse duration), which lasts $1/(10\Omega_{US})$ second, the gate opening occurring at the maximum of the ultrasound wave. The right part shows the ultrasound wave (as a function of the time) and below it, the opening of the gate (or the laser pulse duration), which lasts $1/(10\Omega_{US})$ second, the gate opening occurring at the minimum of the ultrasound wave. The difference between signals in both cases gives the contribution of the ultrasound modulated signal.

An alternating scheme does not use shutter but pulsed laser and ultrasound. The transducer sends a burst wave, and a short laser pulse (shorter than a tenth of the cycle, which means shorter than 100 ns) is sent synchronously (exactly at the time when the shutter should be opened). The result is the same, but it offers two advantages:

it does not necessitate the use of an MCP; and there is no energy loss (all the laser energy is useful).

In this technique, the coherence length of the laser, which must be higher than one meter, limits the laser pulse duration to a minimum pulse width of 3 ns.

The Lock-in camera technique makes use of the recently developed camera, so-called "Lock-in" camera (see Seitz, P., T. Spirig, O. Vietze and K. Engelhardt, "Smart sensing using custom photo-application-specific integrated circuits and charge-coupled device technology", Opt. Eng., 34, 8, 2299, 1995), which makes it possible to directly store several points of the modulation amplitude, and automatically remove the offset due to the static or high-frequency time averaged speckles (see T. Spirig, M. Marley and P. Seitz, "The multitap lock-in CCD with offset subtraction", IEEE trans. electr. dev., 44, 10, 1643, 1997). The best adapted scheme for using this device is the "frequency shifted source" scheme, where $\delta\omega$ is of the order of 10 KHz. Using this procedure, it is possible to directly record the intensity modulation at the frame rate, and without delay between the different phases.

This technique requires a continuous ultrasound wave (not pulse nor burst) and a CW laser. If a single or a few discrete detectors are used, a conventional lock-in amplifier can be used.

The signal processing stage and the algorithms relating to it will now be discussed.

The nature of light in tissues is different whether the probed region is within about 2 cm deep from the air interface or more. Within 2 cm, the light, although diffuse in essence, has a strong ballistic component, and its photons often referred as "snake photons". Beyond this limit, light has lost all ballistic behaviour and its propagation can be considered as isotropic.

In the case of brain probing, this distinction is important since physiologically it also corresponds to different regions. Within 2 to 3 cm from the air interface, the brain consists of a densely blood irrigated region, the cortex. Beyond the cortex, a relatively large region of almost not irrigated tissue, the white matter, almost only diffuses light. Then, in the brain centre region a strongly irrigated region exists, which is of strong clinical interest. Two different methods are therefore appropriate depending on whether one is interested in probing the cortex, with essentially snake photons, or the central brain region, with essentially fully diffuse photons.

Light distribution, as well as light coupling, plays a crucial role in the reliability of the system. According to the region being probed, different light distributions must be applied.

In the case of cortex probing, photons are roughly ballistic, and the photon density decreases exponentially with the distance from the air interface. Back-scattering detection is most appropriate: the light scattered back by the probed region can be detected by means of the same fibre (bundle) through which the light was led into the region or by means of a different fibre (bundle) provided for this purpose.

Figure 8:
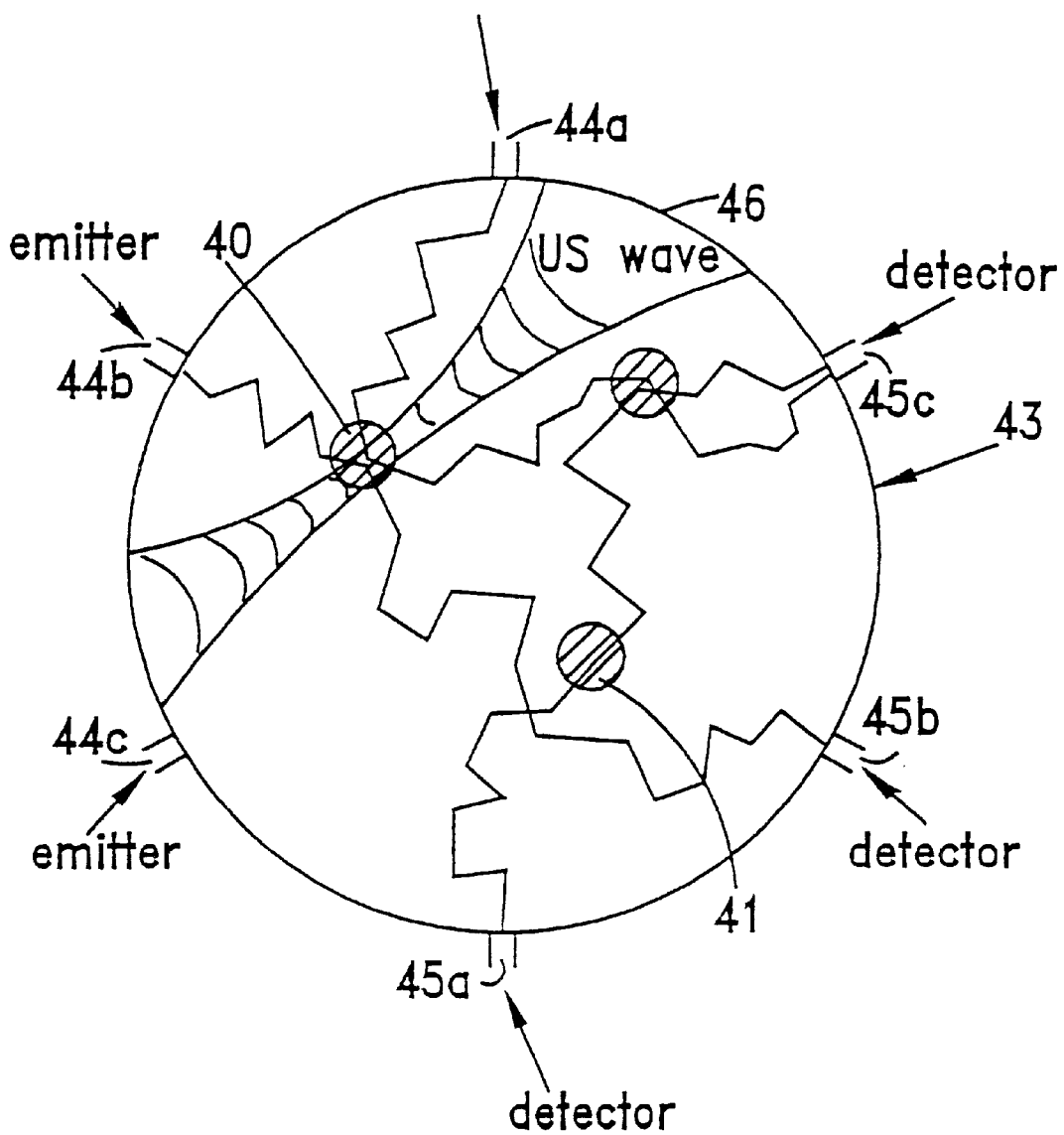
FIG. 8 schematically illustrates a case of in-depth probing of the brain.

In in-depth probing, in contrast with what occurs in ballistic photon systems, the image is not obtained using imaging properties of the light (directivity, focusing ability and so on), but using resolution properties of ultrasonic waves. Light can be considered more or less as a fluid which must fill the entire skull. FIG. 8 schematically illustrates, as an example, the case of three absorbing spheres 40, 41 and 42, within a medium generally indicated at 43. 44a, 44b, and 44c indicate the positions of light emitters and 45a, 45b and 45c indicate the positions of detectors. 46 schematically indicates an ultrasound wave. Ballistic light passing straight through two spheres, e.g. 40 and 41 (or 42), will give no indication on the absorption of each sphere separately, even if an ultrasound wave is focused on one of the spheres—in the figure, sphere 40. This effect can be called "shadowing": it is as if sphere 41 (or 42) were the shadow of sphere 40.

However, diffuse light, which does not follow a straight line, can give information on the absorption of each sphere separately. It is thus more convenient to consider the light as a fluid: the proportion of light going through a particular region within an homogeneous medium is proportional to the volume of this region, provided that the light has been transmitted into the medium in a homogenous enough way. Likewise, in order to avoid "shadowing" of a region by another one, a plurality of sources and detectors must be distributed over the head in a homogeneous enough way. An array of fibres, both for light emission and light detection, is then a good solution.

The use of a liquid crystal valve for improving the signal-to-noise ratio will be discussed now.

In principle, the signal-to-noise ratio can be increased by increasing the amount of light which enters the detector. Practically, since the best detectors have a dynamic range not exceeding $10^6$, it means that, since the modulated signal is very weak ($I_{mod}/I_{not\ mod}$ can be as small as $10^{-6}$), the signal-to-noise is limited due to the saturation of the detector (saturation intensity $I_s$). Here we present an apparatus which allows to significantly reduce this barrier.

The signal that the detector gets is a complex speckle pattern. Let us first analyse this matter. Since the signal is obtained using a heterodyning scheme, it is necessary that the laser has a large enough coherence length. This, of course, implies that a strong speckle is present at the detector, and that the signal is embedded within this speckle. From the speckle theory, it is known that the speckle distribution, shape, size and so on, depend on the distance between the laser and the detector. More precisely, the size at the detector is $\lambda R/D$ where $\lambda$ is the wavelength, R is the distance object detector, and D the detector aperture.

When the ultrasound is focused within the medium, it gives rise to a new kind of optical waves, with a different frequency. This can be considered as a second source of light, within the medium. Consequently, the speckle pattern originating from the ultrasound region, at a shifted frequency, is not, or only slightly, correlated within the general speckle pattern.

Moreover, the modulated signal is very small (in general, between 3 to 5 orders of magnitude) compared to the non-modulated signal.

These two points lead to a device greatly improving the signal-to-noise ratio in the method described above.

The distribution of light intensity in a speckle pattern follows the law:

$$P(I)=1/I_0 \exp{-I/I_0}$$

where P(I) is the probability density to find a speckle (or coherence zone) energy between I and I+dI.

Let us consider now an optical valve situated in front of the detector. The optical valve is a rectangular pixels screen where each pixel can be either transparent to the light or block it. Using a proper optical set-up, the size of each coherence zone (speckle) can be matched to the size of the pixels.

It is possible to image the speckle pattern with a camera. Let us suppose that the camera has N grey levels. Using the probability distribution described above, the amount of speckles with an intensity between 0 and $I_0/N$ is $1-\exp(-I/I_0)=1-\exp(-1/N)\sim 1/N$ if N is large. So for large N, the law is linear. If we now filter out all the speckles with an intensity above $I_0/N$, the not modulated signal is reduced by a factor N, and the noise associated with this signal reduced by a factor $N^{1/2}$.

Figure 9:
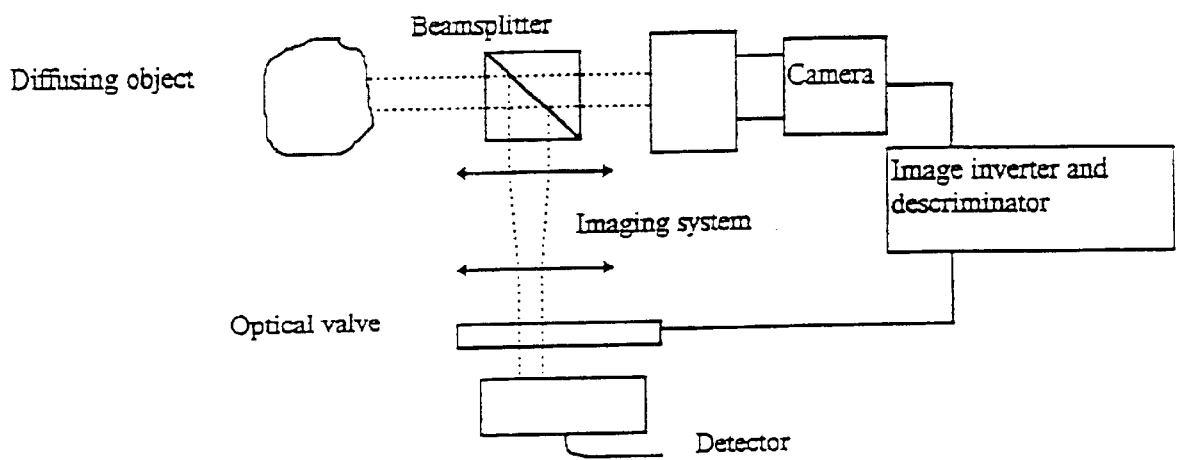
FIG. 9 is a block diagram schematically illustrating a way of filtering out the speckle from an imaged speckle pattern.

Filtering out the speckle can be done using the set-up scheme of FIG. 9.

Light diffused by the sample is split by a beam-splitter into two arms:

A small amount is sent to a monochrome camera. The image out of the camera is then inverted (black regions become white, and vice versa), and discriminated so that only the brighter level remains white, all the other becoming black (binary image). This image is sent to an optical valve (such as a liquid crystal monochrome display whose backplane has been removed), which reproduces the binary image. This binary image consists of transparent and opaque regions on the screen.

Most of the light is sent (after the beam-splitter) directly to the optical valve, after proper imaging, so that the image displayed on the optical valve and the image coming from the beam-splitter coincide exactly. The darkest part of the image coming from the beam-splitter is transmitted by the optical valve, since this region is transparent. However, the bright regions are blocked.

If the optical valve has N grey levels, N being chosen so that $I_0/N$ is larger than the amplitude of the modulated signal, thus the non-modulated signal maximum intensity on the detector is reduced by a factor N. Since the modulated signal speckle is not correlated with the non-modulated signal speckle, the intensity of the modulated signal is not modified in average.

Because only 1/N of the pixels are used, both the modulated and non-modulated signals are reduced by another factor N. Consequently, on the detector, the non-modulated signal is reduced by a factor $N^2$, whereas the modulated signal is reduced by a factor N. By increasing the intensity by a factor $N^2$, the non-modulated signal on the detector comes back to its initial value, whereas the modulated signal is increased by a factor N, so the signal-to-noise is increased by a factor N. This technique is particularly well adapted to photomultiplier or photon counting techniques, where the sensitivity is very high, the noise is quantum noise, and the dynamic range is quite high.

As a matter of example, such a technique with an 8-bit optical valve would theoretically increase the signal-to-noise ratio by a factor 128.

The non-linear effects for improving both contrast and resolution will now be discussed.

In order to improve the contrast and the resolution of the method, it is possible to use the second harmonic of the interaction ultrasound-light. It is well known from the Raman-Nath theory, that the interaction between ultrasound and light is not linear. At low ultrasound powers, the interaction increases linearly when increasing the ultrasound power. However, this interaction reaches an absolute value for the Raman-Nath parameter value of 1.4, and then decreases. Simultaneously, a second-order interaction starts increasing, giving rise to a Doppler shift of $2\Omega_{US}$. At a Raman-Nath parameter value between 2 and 3, this interaction is maximal, and the first-order interaction almost disappears. Increasing the ultrasound power even more gives rise to the third, fourth, and so on harmonics of the ultrasound.

When the ultrasound wave is focused, the ultrasound amplitude at the focal point is larger than in the other regions of the beam. Interaction between the ultrasound wave and the light varies along the ultrasound propagation axis. If the ultrasound power is large enough, there will be a non-linear interaction at the focal region, whereas the interaction will be linear outside the focal region. It is well known that the interaction between ultrasound and light can give rise to a Doppler shift of the light at $\Omega_{US}$, $2\Omega_{US}$ $3\Omega_{US}$, etc., the degree of the highest harmonic depending on the ultrasound amplitude. By properly choosing said amplitude, it is possible to obtain a $2\Omega_{US}$ Doppler shift at the focal region, while obtaining $\Omega_{US}$ shift in the rest of the beam. The signal detected at $2\Omega_{US}$ thus comes from the focal region alone. This improves the localisation and the resolution of the method.

When changes at the second harmonic are originating only from the focal region, the contrast is drastically increased since background signal originating from linear ultrasound-light is not present). Moreover, the resolution is better by a factor 2. This is due to the fact that the resolution is linear with the ultrasound frequency. Using the second harmonic of the interaction ultrasound light is equivalent to using the first harmonic of an ultrasound wave with twice the frequency, which explains the gain in resolution.

While embodiments of the invention have been described by way of illustration, it will be apparent that many modifications, variations and adaptations may be made therein by persons skilled in the art, without departing from the spirit of the invention or exceeding the scope of the claims.

What is claimed is:

1. A method for determining a degree of oxygenation of hemoglobin in probed regions of a human body, which comprises the steps of: successively selecting a plurality of probed regions and for each
    (a) irradiating said probed region with diffuse near-infrared laser light;
    (b) generating at least one ultrasound wave, chosen from among continuous, pulse or burst waves;
    (c) focusing said ultrasound wave in at least a focus region of said probed region, to modulate and frequency-shift said light in said probed region;
    (d) detecting said light, modulated by said ultrasound wave, emerging from said focus region;
    (e) determining a change in the absorption of said modulated light caused by local changes in said probed region; and
    (f) calculating from said change in the absorption the change in the degree of hemoglobin oxygenation in the probed region.

2. A method according to claim 1, further comprising monitoring blood volume in said probed regions by irradiating said probed regions with light at an isosbestic point at which oxyhemoglobin and deoxyhemoglobin have equal absorption of said light modulated by said ultrasound wave.

3. A method according to claim 1, wherein the light has a wavelength in the 690 to 900 nm range.

4. A method according to claim 1, wherein the irradiation is carried out with light having more than one wavelength.

5. A method according to claim 1, wherein the irradiation is carried out with light having at least two wavelengths, one below and one above an isosbestic point.

6. A method according to claim 1, further comprising detecting the light not modulated by the ultrasound wave emerging from the probed region together with the light modulated by the ultrasound wave.

7. A method according to claim 1, wherein the change in the absorption of the ultrasound modulated light in the probed region, due to changes in the oxygenation state of the hemoglobin, is represented by an analog signal, which method further comprises transforming said analog signal to a digital signal, to be processed.

8. A method according to claim 7 wherein said digital signal is visualized.

9. A method according to claim 1, wherein said probed regions are part of the brain of a human body.

10. A method according to claim 1, wherein the at least one ultrasound wave has a frequency in a range from 0.2 to 2 MHz.

11. A method according to claim 1, wherein the probed regions are not a part of the brain and a maximum ultrasound frequency is in a range from 8 to 16 MHz.

12. A method according to claim 1, wherein the light modulated by the ultrasound is expressed by a heterodyne signal created by a technique selected from among detection modulation and source modulation.

13. A method according to claim 1, wherein the light modulated by the ultrasound, emerging from the probed regions is detected by a technique chosen from among time sampling and lock-in CCD technique.

14. A method according to claim 1, wherein the change in the absorption of the said modulated light caused by local change in said probed region is determined by determining intensities of said light modulated by said ultrasound and of light not modulated by said ultrasound and calculating their ratio.

15. A method according to claim 1, wherein the change in the absorption of said modulated light caused by local changes in said probed region is determined by determining the intensity of said light at $\omega_L$ and of said light at $\omega_L + \Omega_{us}$, wherein $\omega_L$ is the frequency of the irradiating light and $\Omega_{us}$ is the frequency of the modulating ultrasound.

16. A method according to claim 1, wherein said at least one ultrasound wave has an intensity chosen so as to obtain a $2\Omega_{us}$ shift in frequency of said light at the focal region, while obtaining $\Omega_{us}$ shift in frequency outside said focal region.

17. Apparatus for determining the oxygenation level of hemoglobin in a probed region of a human body, which comprises: at least one light generator; optical fiber bundles and coupling devices optically connecting said generator to the part of the body comprising said probed region; at least a transducer for generating an ultrasound wave and a focus of said ultrasound wave in said probed region; optical fibers which collect light that has passed through the probed region and through said focus of said ultrasound wave and transmit it to at least one receiving instrument, and means for elaborating the signals generated by said receiving instrument, said apparatus further comprising a beam splitter, a camera, a discriminator and a liquid crystal valve situated in front of said at least one receiving instrument, in order to increase signal to noise ratio.

18. Apparatus according to claim 17, wherein the receiving instrument is a detector array.

19. Apparatus according to claim 18, wherein the detector array is chosen from among CCD cameras, photomultipliers, or diode detectors.

20. Apparatus according to claim 17, wherein the means for elaborating the signals comprise a digital signal processor and a signal processor and visualizing apparatus.

21. Apparatus according to claim 17, for examining a brain of the human body, wherein the optical fibers are adapted to be directly set on the head at a plurality of positions and the ultrasound wave is generated and focused by a transducer when tightly pressed against the skull.

22. Apparatus according to claim 17, for examining a brain of the human body, wherein the optical fibres are adapted to be directly set on the head at a plurality of positions and the ultrasound wave is generated and focused by a plurality of transducers adapted to be spread over a large region of the skull, arranged so that the ultrasonic waves of each of the transducers are focused in the same region on the brain.

23. Apparatus according to claim 17, wherein the transducers generate ultrasound waves that are phase-arrayed to produce a strong focus in the brain.

24. Apparatus according to claim 17, comprising a plurality of light generators and of detectors, disposed so as to remove any possible shadowing of a part of a probed region on another probed region.

25. A method for determining a degree of oxygenation of hemoglobin in a probed region of a human body, which comprises the steps of:
(a) irradiating a probed region of the human brain with diffuse near-infrared laser light;
(b) generating at least one ultrasound wave, chosen from among continuous, pulse or burst waves;
(c) focusing said ultrasound wave in at least a focus region of said probed region, to modulate and frequency-shift said light in said probed region;
(d) detecting said light, modulated by said ultrasound wave, emerging from said focus region;
(e) determining a change in the absorption of said modulated light caused by local changes in said probed region; and
(f) calculating from said change in the absorption the change in the degree of hemoglobin oxygenation in said probed region.

26. A method according to claim 25, further comprising monitoring blood volume in said probed region by irradiating said probed region with light at an isosbestic point at which oxyhemoglobin and deoxyhemoglobin have equal absorption of said light modulated by said ultrasound wave.

27. A method according to claim 25, wherein said light has a wavelength in the range of 690 to 900 nm.

28. A method according to claim 25, wherein said irradiation is carried out with light having more than one wavelength.

29. A method according to claim 25, wherein the irradiation is carried out with light having at least two wavelengths, one below and one above an isosbestic point.

30. A method according to claim 25, further comprising: detecting the light not modulated by the ultrasound wave emerging from the probed region together with the modulated light.

31. A method according to claim 25, wherein the change in the absorption of said ultrasound modulated light in said probed region of the brain, due to changes in oxygenation state of the hemoglobin, is represented by an analog signal.

32. A method according to claim 31, further comprising the step of transferring said analog signal to a digital signal, to be processed.

33. A method according to claim 32, wherein said digital signal is visualized.

34. A method according to claim 25, wherein the at least one ultrasound wave has a frequency in a range from 0.2 to 2 MHz.

35. A method according to claim 25, wherein a maximum ultrasound frequency is in a range from 8 to 16 MHz.

36. A method according to claim 25, wherein the light modulated by the ultrasound is expressed by a heterodyne signal created by a technique selected from among detection modulation and source modulation.

37. A method according to claim 25, wherein said light modulated by the ultrasound wave emerging from the probed region is detected by a technique chosen from time sampling and lock-in CCD technique.

38. A method according to claim 25, wherein the change in the absorption of said modulated light caused by local change in said probed region is determined by determining intensities of said light modulated by said ultrasound and of light not modulated by said ultrasound and calculating their ratio.

39. A method according to claim 25, wherein the change in the absorption of said modulated light caused by local change in said probed region is determined by determining intensity of said light at $\omega_L$ and of said light at $\omega_L + \Omega_{us}$, wherein $\Omega_L$ is the frequency of the irradiating light and $\Omega_{us}$ is the frequency of the modulating ultrasound.

40. A method according to claim 25, wherein said at least one ultrasound wave has an intensity chosen so as to obtain a $2\Omega_{us}$ shift in frequency of said light at the focal region, while obtaining $\Omega_{us}$ shift in frequency outside said focal region.

41. A method for determining a degree of oxygenation of hemoglobin in a probed region of a human body, which comprises the steps of:
(a) irradiating the probed region with diffuse near-infrared laser light;
(b) generating at least one ultrasound wave, chosen from among continuous, pulse or burst waves;
(c) focusing said ultrasound wave in at least a focus region of said probed region, to modulate and frequency-shift said light in said probed region;
(d) detecting said light, modulated by said ultrasound wave, emerging from said focus region;
(e) determining the change in the absorption of said modulated light caused by local changes in said probed region; and
(f) calculating from said change in the absorption the change in the degree of hemoglobin oxygenation in said probed region;
wherein the light modulated by said ultrasound emerging from the said probed region is detected by a technique chosen from among time sampling and lock-in CCD technique.

42. A method according to claim 41, further comprising monitoring blood volume in said probed region by irradiating said probed region with light at an isosbestic point at which oxyhemoglobin and deoxyhemoglobin have equal absorption of said light modulated by said ultrasound wave.

43. A method according to claim 41, wherein said light has a wavelength in the range of 690 to 900 nm.

44. A method according to claim 41, wherein said irradiation is carried out with light having more than one wavelength.

45. A method according to claim 41, wherein the irradiation is carried out with light having at least two wavelengths, one below and one above an isosbestic point.

46. A method according to claim 41, further comprising: detecting light not modulated by the ultrasound wave emerging from the probed region together with the modulated light.

47. A method according to claim 41, wherein the change in the absorption of said ultrasound modulated light in said probed region, due to changes in oxygenation state of the hemoglobin, is represented by an analog signal.

48. A method according to claim 47, further comprising the step of transferring said analog signal to a digital signal, to be processed.

49. A method according to claim 48, wherein said digital signal is visualized.

50. A method according to claim 41, wherein the at least one ultrasound wave has a frequency in a range from 0.2 to 2 MHz.

51. A method according to claim 41, wherein a maximum ultrasound frequency is in a range from 8 to 16 MHz.

52. A method according to claim 41, wherein the light modulated by the ultrasound is expressed by a heterodyne signal created by a technique selected from among detection modulation and source modulation.

53. A method according to claim 41, wherein the change in the absorption of said modulated light caused by local change in said probed region is determined by determining intensities of said light modulated by said ultrasound and of light not modulated by said ultrasound and calculating their ratio.

54. A method according to claim 41, wherein the change in the absorption of said modulated light caused by local change in said probed region is determined by determining intensity of said light at $\omega_L$ and of said light at $\omega_L + \Omega_{us}$, wherein $\omega_L$ is the frequency of the irradiating light and $\Omega_{us}$ is the frequency of the modulating ultrasound.

55. A method according to claim 41, wherein said at least one ultrasound wave has an intensity chosen so as to obtain a $2\Omega_{us}$ shift in frequency of said light at the focal region, while obtaining $\Omega_{us}$ shift in frequency outside said focal region.

* * * * *

UNITED STATES PATENT AND TRADEMARK OFFICE
CERTIFICATE OF CORRECTION

PATENT NO. : 6,738,653 B1
DATED : May 18, 2004
INVENTOR(S) : Bruno Gad Sfez et al.

It is certified that error appears in the above-identified patent and that said Letters Patent is hereby corrected as shown below:

Column 9,
Line 23, delete "$\Delta 72$", and insert therefor -- $\Delta \eta$ --.
Line 24, after "," insert -- where L --.

Column 11,
Line 51, delete "$\tau$" and insert therefor -- $\pi$ --.

Column 16,
Line 52, after "collect" insert -- the --.

Column 17,
Line 10, after "transducers" insert -- which are --.

Column 18,
Line 21, delete "$\Omega_L$" and insert therefor -- $\omega_L$ --.

Signed and Sealed this

Seventh Day of September, 2004

JON W. DUDAS
*Director of the United States Patent and Trademark Office*